US00PP23076P2

(12) United States Plant Patent
Noodelijk

(10) Patent No.: US PP23,076 P2
(45) Date of Patent: Sep. 25, 2012

(54) ***CELOSIA* PLANT NAMED 'SPITENZ'**

(50) Latin Name: *Celosia argentea*
Varietal Denomination: Spitenz

(75) Inventor: Robert Noodelijk, Woubrugge (NL)

(73) Assignee: Floritec Breeding, BV, Amsterdam (NL)

( * ) Notice: Subject to any disclaimer, the term of this patent is extended or adjusted under 35 U.S.C. 154(b) by 0 days.

(21) Appl. No.: 13/068,074

(22) Filed: May 2, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para
(74) *Attorney, Agent, or Firm* — Jondle & Associates, P.C.

(57) ABSTRACT

A *Celosia* plant named 'Spitenz' characterized by its many purple colored spikes, prolific branching, foliage mainly at the bottom of the plant, a compact and symmetrical plant habit, and a short response time of approximately 6.5 weeks is disclosed.

3 Drawing Sheets

Genus and species: *Celosia argentea.*
Variety denomination: 'Spitenz'.

BACKGROUND OF THE NEW PLANT

The present invention comprises a new and distinct variety of *Celosia* plant, botanically known as *Celosia argentea*, and hereinafter referred to by the variety name 'Spitenz'. This new variety produces many medium sized spikes with purple colored individual blooms and a blooming period of about eight weeks.

The new variety 'Spitenz' originated from an open pollination conducted in May 2008 among groups of un-named and unpatented proprietary *Celosia* varieties maintained under the control of the inventor for breeding purposes. The new and distinct variety was discovered and selected as a single plant in a greenhouse in Monster, The Netherlands in March 2009.

The new variety 'Spitenz' was first asexually reproduced by vegetative cuttings in a greenhouse in Monster, The Netherlands in July 2009 and has been asexually reproduced for 1 and a half years. The new variety 'Spitenz' has been found to retain its distinctive characteristics through successive asexual propagations.

SUMMARY OF THE INVENTION

The following are the most outstanding and distinguishing characteristics of the new variety when grown under normal horticultural practices in Monster, The Netherlands.

1. Purple spiked-type inflorescences having many spikes per branch;
2. Prolific branching;
3. Compact symmetrical plant habit; and
4. Foliage located all over the stem to the bottom of the plant.

DESCRIPTION OF THE PHOTOGRAPHS

This new *Celosia* plant is illustrated by the accompanying photographs which show blooms and foliage of the plant. The colors shown are as true as can be reasonably obtained by conventional photographic procedures. The photographs are of a plant that has been in bloom for approximately 3 weeks.

DESCRIPTION OF THE NEW VARIETY

Figure 1:
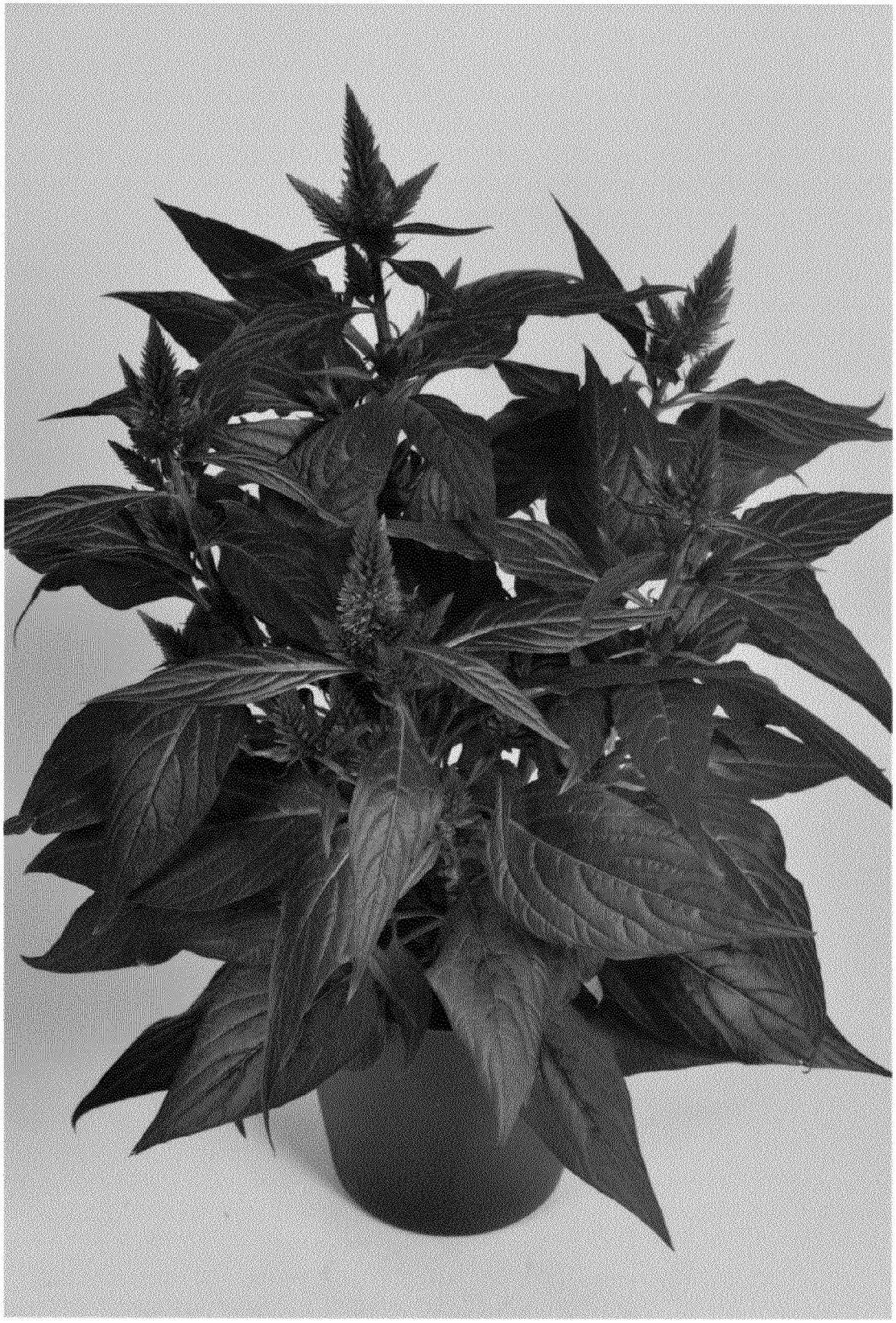
FIG. 1 shows the plant habit including the foliage and inflorescences.
Figure 2:
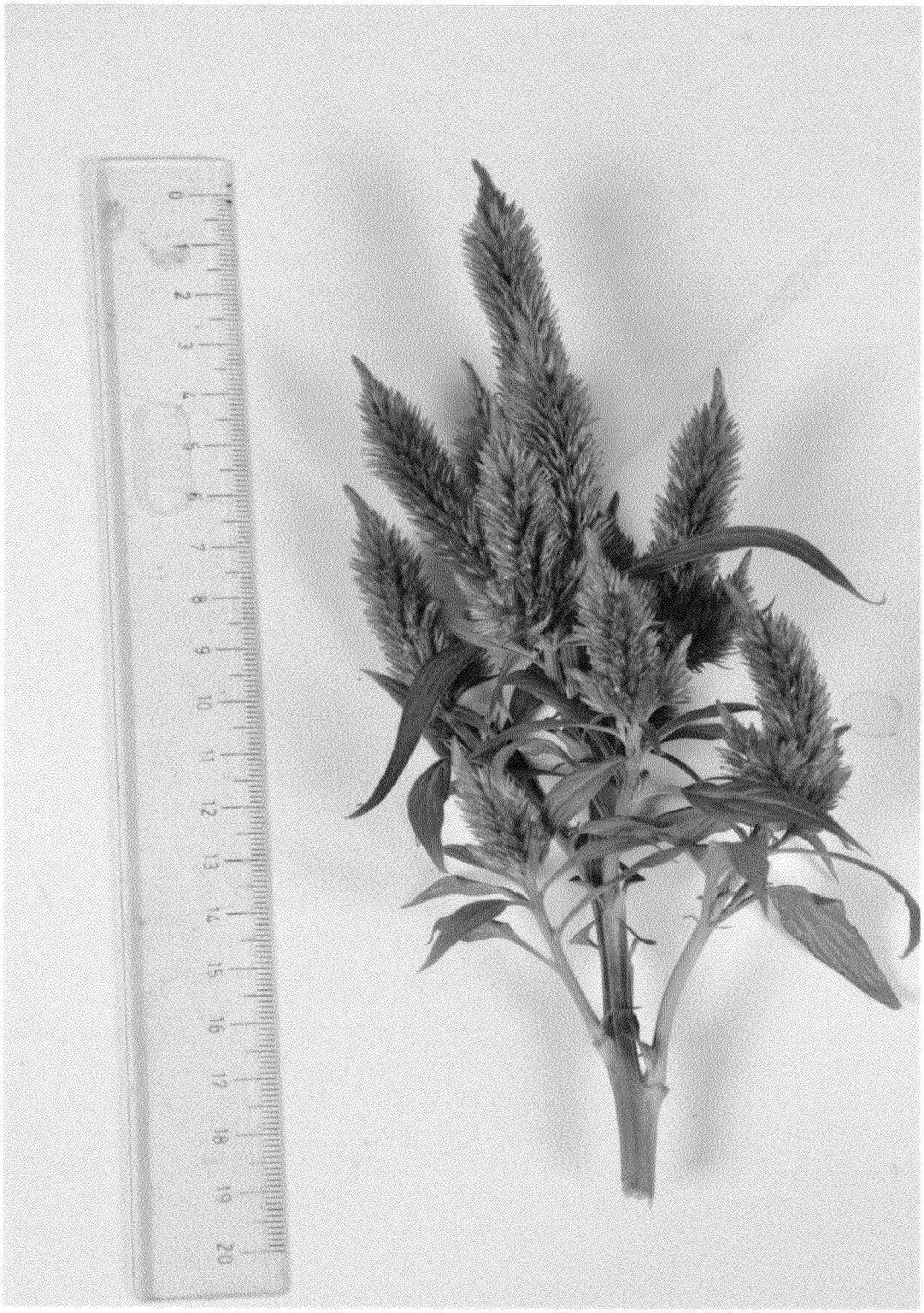
FIG. 2 is a close-up of the new variety 'Spitenz', showing individual spikes and inflorescences per branch.
Figure 3:
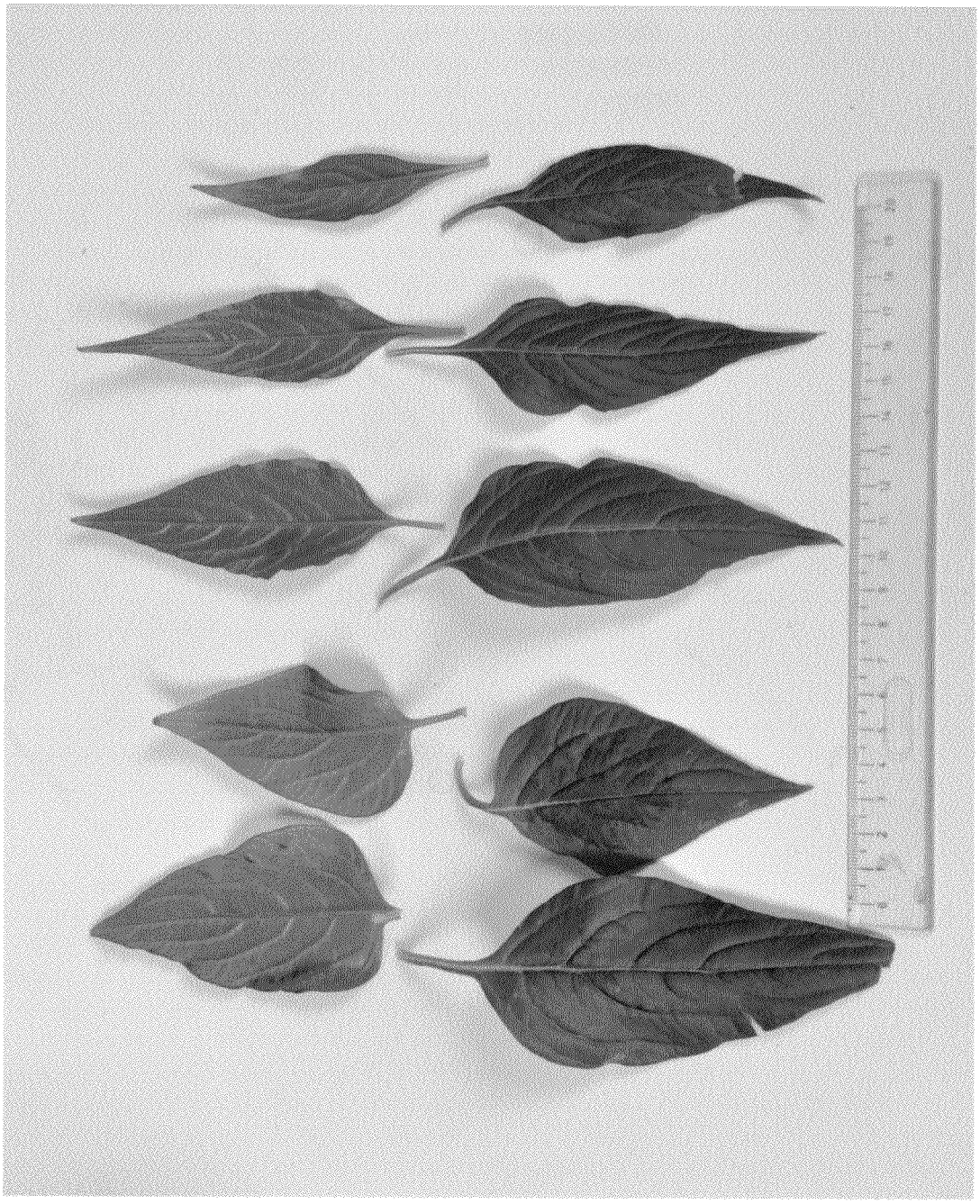
FIG. 3 is a close-up of the upper and under surfaces of the leaves of the new variety 'Spitenz'.

The following detailed descriptions set forth the distinctive characteristics of 'Spitenz'. The data which define these characteristics were collected from asexual reproductions carried out in Monster, The Netherlands. The plant history was taken on un-pinched plants of 8 to 10 weeks old, which were grown in 10 cm pots in a greenhouse in Monster, The Netherlands under controlled day length and temperatures. Growth retardants were used weekly. The color readings were determined under natural light. Color references are to The R.H.S. Colour Chart of The Royal Horticultural Society of London (R.H.S.), 1995 Edition.

DETAILED BOTANICAL DESCRIPTION

Classification:
- *Botanical.*—*Celosia argentea.*
- *Common name.*—Cockscomb, Woolflower, Feathery Amaranth.
- *Denomination.*—'Spitenz'.

Plant:
- *Form.*—Rounded.
- *Growth habit.*—Spreading.
- *Growth rate.*—Fast.
- *Height.*—30.0 to 32.0 cm (using weekly growth retardant).
- *Width.*—20.0 to 25.0 cm (using weekly growth retardant).

Branches:
- *Stem.*—Color: RHS 147C (Green). Strength: Strong. Brittleness: Branches are not brittle. Anthocyanin coloration: Present.

*Length of lateral branch* (*from top to bottom*).—17.0 cm to 20.0 cm.
*Diameter of lateral branch.*—0.4 cm.
*Lateral branch color*.—RHS 147C (Green).
*Lateral branch attachment*.—Petiolate.
*Branching*.—Average number of lateral branches: Prolific, with 4 to 6 breaks after pinching.

Leaves:
*Color*.—Upper surface: RHS 137B (Green and partially turning RHS 59A (Red) with age. Lower surface: RHS 147C (Green). Veins: RHS 45B (Red).
*Size*.—General: Medium.
*Immature foliage*.—Length: 9.0 cm. Width: 2.0 cm.
*Mature foliage*.—Length: 15.0 cm. Width: 5.5 cm.
*Quantity per lateral branch.*—6 to 8.
*Shape*.—Cordiform.
*Apex*.—Acute.
*Base*.—Attenuate.
*Margin*.—Entire.
*Texture*.—Upper surface: Leathery. Lower surface: Leathery.
*Venation arrangement*.—Pinnate.

Inflorescence:
*Type*.—Many small individual tubular blooms arranged together in a spiked-type inflorescence.
*Height.*—1 week old spike: 3.0 to 3.5 cm. 3 week old spike: 7.0 to 8.0 cm.
*Number of spikes per branch*.—Approximately 10 per branch.
*Number of blooms per spike.*—1 week old spike: Approximately 75 to 80. 3 week old spike: Approximately 160 to 180.
*Performance on the plant* (*blooming period*).—8 weeks.
*Fragrance*.—Absent.
*Tonality from distance*.—A very rich flowering compact *Celosia* pot plant.
*Discoloration to color*.—None.
*Peduncle*.—Length: 5.0 cm to 7.0 cm. Diameter: 0.3 cm. Color: RHS 147C (green).
*Response time.*—6.5 to 7 weeks.

Florets:
*Number of petals per floret.*—5.
*Petal texture* (*both surfaces*).—Papery.
*Apex*.—Acuminate.
*Margin*.—Entire.
*Length.*—0.6 cm.
*Width.*—0.2 cm.
*Color*.—(both surfaces): RHS 78A (Purple).

Reproductive organs:
*Stamen*.—Width: Very thin, 0.05 cm. Color: RHS 78A (Purple). Pollen amount: Sparse; appears at a very late stage. Pollen color: RHS 155A (White).
*Pistil*.—Style appearance: Very thin. Style color: RHS 78A (Purple). Style length: 0.6 cm. Stigma color: RHS 78A (Purple). Stigma width: 0.1 cm.

Fruit/seed set: Not observed.

COMPARISON WITH COMMERCIAL VARIETIES

The new variety 'Spitenz' differs from the commercial *Celosia* variety 'Caracas' (unpatented) in that 'Spitenz' is more compact and has a plant habit that is more symmetrical and more freely branching than 'Caracas' (4 to 6 branches in comparison to an average of 3 for 'Caracas'). Further, the new variety 'Spitenz' has more foliage towards to bottom of the plant than 'Caracas', and has many more spikes per branch than 'Caracas'. The new variety 'Spitenz' has foliage that is narrower than that of 'Caracas' and has a shorter response time of 6.5 weeks in comparison to the response time of 'Caracas', which averages 7.5 weeks.

I claim:

1. A new and distinct variety of *Celosia* plant named 'Spitenz' as described and shown herein.

* * * * *